United States Patent [19]

Karami

[11] Patent Number: 4,585,447
[45] Date of Patent: Apr. 29, 1986

[54] DISPOSABLE DIAPER WITH INTERSECTING STRESSED CROTCH AND WAIST SEALS

[75] Inventor: Hamzeh Karami, Weston, Mass.

[73] Assignee: Colgate-Palmolive Company, New York, N.Y.

[21] Appl. No.: 723,380

[22] Filed: Apr. 15, 1985

[51] Int. Cl.$^4$ ............................................. A61F 13/16
[52] U.S. Cl. ............................................. 604/385 A
[58] Field of Search ..................... 604/385, 385 A, 358

[56] References Cited

U.S. PATENT DOCUMENTS

| | | | |
|---|---|---|---|
| 4,325,372 | 4/1982 | Teed | 604/385 |
| 4,337,771 | 7/1982 | Pieniak et al. | 604/385 A |
| 4,397,646 | 8/1983 | Daniels et al. | 604/385 A |
| 4,402,688 | 9/1983 | Julemont | 604/385 A |

Primary Examiner—John D. Yasko
Attorney, Agent, or Firm—Herbert S. Sylvester; Murray M. Grill; Norman Blumenkopf

[57] ABSTRACT

A disposable diaper having elasticized crotch seals and an elasticized waist seal formed from elastic members secured to the backing sheet. The elastic members physically intersect each other and are under such tension so as to provide an initial stretching of the elastic members extending substantially at right angles to each other thereby maximizing the comfort of an infant wearing the disposable diaper while maintaining a boat-like shape before application on an infant with the ears in a raised position. The elastic members may be spaced from the edge of the pad or may overlie the front or back surface of the pad to minimize leakage.

4 Claims, 1 Drawing Figure

U.S. Patent  Apr. 29, 1986  4,585,447
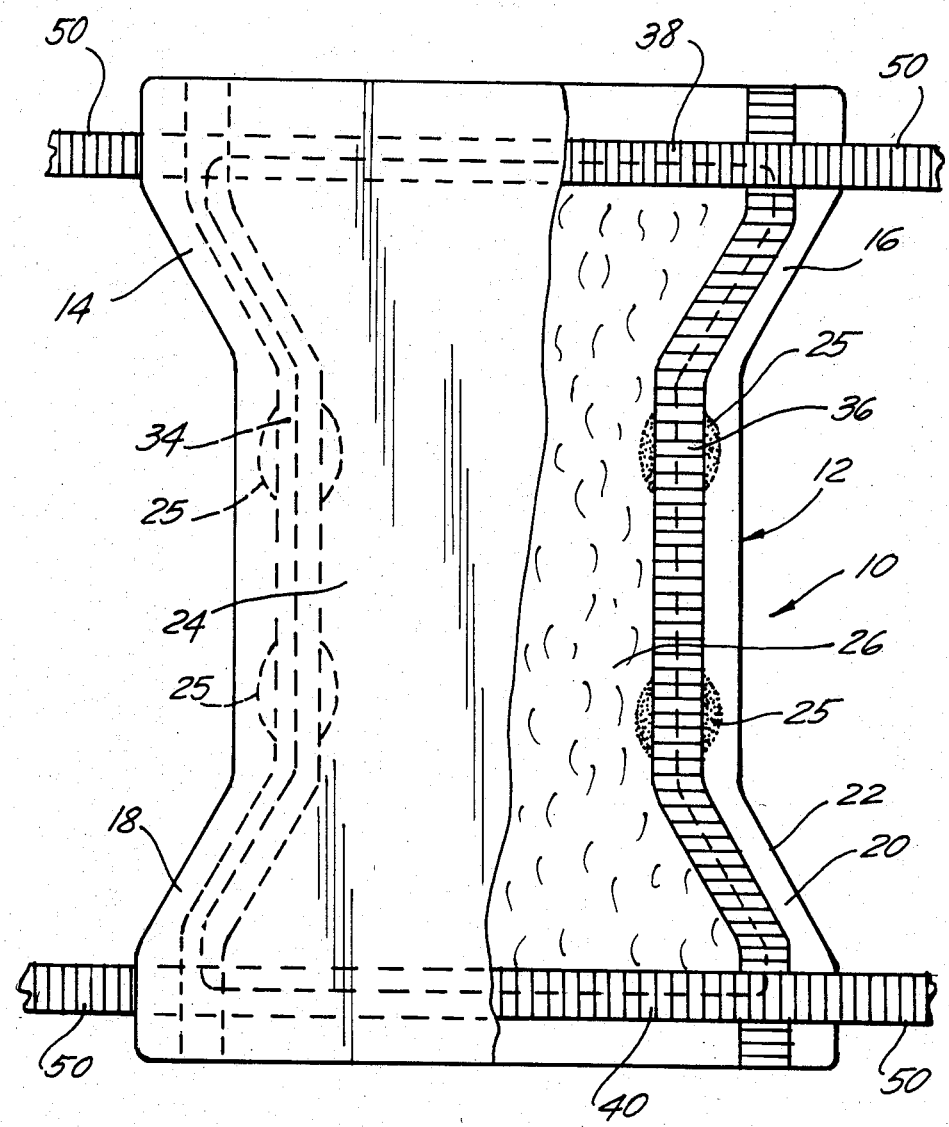

DISPOSABLE DIAPER WITH INTERSECTING STRESSED CROTCH AND WAIST SEALS

BACKGROUND OF THE INVENTION

1. Field of the Invention

This invention relates to disposable diapers and, more particularly, to a contoured diaper having crotch seals and/or waist seals.

2. Description of the Prior Art

In the past, elasticized contoured diapers have been developed such as that disclosed in the Buell U.S. Pat. No. 3,860,003, issued Jan. 14, 1975, for "Contractable Side Portions for Disposable Diapers," wherein elastic strips are secured to the crotch portions of the diaper and spaced at least ⅜ inch from the absorbent pad to form elasticized crotch seals for securement over the legs of the infant to prevent loss of fluid from the interior of the diaper along the legs of the infant. The elasticized strips are placed more than ⅜ inch from the absorbent pad to provide a wide contractable side flap for improved containment.

In U.S. Pat. No. 4,050,462 to Woon and Endres elastic strips are provided in the crotch area of the diaper whereby a plurality of gross transverse rugosities across the width of the crotch section are formed to improve the absorbent capacity at the crotch area. However, it has been found that these pleats may act as a channel resulting in excessive diaper leakage and the pleats in the crotch area make the infant's bottom uncomfortable when sitting, especially while the diaper is not saturated.

United Kingdom Pat. No. 2,023,431 discloses a contoured disposable diaper having elasticized waist bands and crotch seals.

None of these patents show a disposable diaper with the crotch and waist band elastic members physically intersecting on the ears of a contoured diaper to hold the ears in a raised position prior to placement on an infant.

Elasticized waist seals are old and well known for various garments including diapers. These waist seals have been for the purpose of maintaining the garment in place and have not been for the two additional purposes of the present invention so as to provide for a fluid barrier while also providing for a cooperative effect in conjunction with the crotch seals whereby the crotch seals provide a direct initial stress on the physically intersecting waist seals with the waist seals providing an initial stress for the crotch seals. Additionally, the elastic waist seals may be structured to serve as a means for securing the diaper as well. The ears are also maintained in a raised position.

SUMMARY OF THE INVENTION

The present invention overcomes the disadvantages of the prior art diapers by providing for elastic members along the opposite sides of the diaper and along the waist portion of the diaper whereby crotch seals and waist seals are formed which physically intersect and coact to provide direct initial stress on each other because of the direct tension they place on the intersecting elastic member.

In carrying out the invention, a substantially hour-glass shape diaper is formed having a backing sheet, an absorbent pad on the backing sheet, and a top sheet overlying the absorbent body. Opposed side elastic members are secured to the backing sheet as well as an opposed waist elastic member forming respectively crotch seals and a waist seal which physically intersect each other on the ears and cooperate to place a direct initial stress and stretch on the waist seal and crotch seal respectively while holding the ears raised in a positive manner instead of allowing them to flap backward as they do when the elastic members do not intersect on the ears. The elastic crotch and waist seals may serve as fluid barriers particularly when they overlie the absorbent pad. The waist seal or seals may also be extended beyond the side edges of the diaper to provide integral means in place of the conventional separate tape tab means for securing the diaper around the infant.

BRIEF DESCRIPTION OF THE DRAWING

The FIGURE is a plan view of a disposable diaper constructed in accordance with one concept of the present invention.

DETAILED DESCRIPTION OF THE INVENTION

With continuing reference to the accompanying drawing, wherein like reference numerals designate similar parts throughout the various views, reference numeral 10 generally designates an elasticized and contoured diaper constructed in accordance with the concept of the present invention. The diaper 10 is of an hour-glass configuration for a crotch area 12 and four portions of greater width defining ears 14, 16, 18 and 20. The diaper includes a backing sheet 22 of an impervious polyethylene or polypropylene or the like. A top sheet 24 preferably of non-woven polyethylene or polypropylene fibers or a combination thereof is secured to the backing sheet 22 along the peripheral edges of the diaper 10 preferably with adhesive, either hot melt or pressure-sensitive or by heat sealing. An absorbent pad 26 is disposed between the top sheet 24 and the backing sheet 22 and may be of wood fluff or the like. Wadding sheets may be provided as desired.

A first pair of elasticized strips 34 and 36 are provided. The backing sheet 22 is coated with adhesive lines or spots 25 on its top surface thereof and the strips 34 and 36, in stretched state, are thus bonded to the backing sheet 22 along the entire length of the diaper and conform generally to the contoured shape of the diaper with a portion of each strip 34 and 36 thereof overlying the pad 26 and optionally entirely overlying the pad at the ears 14, 16, 18 and 20. The strips 34 and 36 are secured by the adhesive preferably in the crotch area with the ends which overlie the ears 14, 16, 18 and 20 to the ends of the diaper.

A second pair of elasticized members, in stretched state, indicated at 38 and 40 are bonded to the backing sheet 22 and are water impervious forming fluid barriers and are secured between the backing sheet 22 and the top sheet 24 either by adhesive or heat sealing and serve to form waist seals. The elastic members 38 and 40 physically intersect, overlie and are bonded by adhesive to the elastic members 34 and 36.

The elastic strips 38 and 40 extend at nearly right angles to the elasticized strips 34 or 36 and are bonded to the backing sheet 22 with a slight initial tension thereon. Thus, the strips 38 and 40 and the strips 34 and 36 cooperate to place a direct initial stress and stretch to the respective crotch seals and waist seals formed thereby and thus assure a more comfortable and better fit while holding the ears 14, 16, 18 and 20 in a raised position for convenient access thereto in placing the diaper on an infant. The strips 38 and 40 and the strips 34 and 36 are preferably made of a waterproof material further assuring fluid seals. The desirability of the ears 14, 16, 18 and 20 being raised is enhanced by the fact that the waist elastic members 38 and 40 may extend beyond the side edges of the diaper as at 50 and may be coated with a pressure-sensitive adhesive protected by a peelable release sheet. This permits the extensions 50 to function as convenient attached elasticized fasteners for adjustably securing the diaper on the infant.

The diaper in its initial condition, because of the prestretched condition of the members, assumes a boat-like configuration. In prior contoured disposable diapers, the ears are not supported and will tend to flop downwardly making it less convenient to use tape fasteners to attach the diaper on the infant. Because the prestretched elastic members 34, 36 and 38, 40 intersect on the ears, the ears are raised and the extensions 50 are easily engaged and used to fasten the diaper on the infant. If conventional tape fasteners are used, and no extensions 50 are provided, the raised position of the ears facilitates placement of the diaper on an infant.

What is claimed is:

1. A disposable diaper comprising a backing sheet, an absorbent pad on said backing sheet, said absorbent pad being of an hour-glass shape defining pairs of ears spaced from a crotch area, a top sheet overlying said absorbent pad, said top sheet being secured to said backing sheet on at least two opposite peripheral edges thereof, a first pair of elastic members, adhesive means securing said first pair of elastic members to said backing sheet along two opposite side edges thereof to define crotch seals with said side elastic members overlying said ears, and a second pair of elastic members secured to said backing sheet along the end edges to define waist seals with said second pair of elastic members overlying said ears and physically intersecting and bonded to said first pair of elastic members and cooperating to place direct initial stress and stretch on said waist seals and crotch seals respectively and to hold said ears in a raised position, said second pair of elastic members having ends extending beyond said diaper forming elastic extensions held in a raised position, said extensions being coated with a pressure-sensitive adhesive and having release sheets thereon, said extensions forming securement means for securing said diaper about an infant.

2. A disposable diaper according to claim 1, wherein said top sheet is heat sealed to said backing sheet.

3. A disposable diaper according to claim 1, wherein said pairs of elastic members are waterproof forming fluid barriers.

4. A disposable diaper comprising a backing sheet, an absorbent pad on said backing sheet, said absorbent pad being of a hour-glass shape defining pairs of ears spaced from a crotch area, a top sheet overlying said absorbent pad and secured to said backing sheet, opposed side elastic members, adhesive means securing said side elastic members to said backing sheet along two opposite side edges thereof to define crotch seals with said side elastic members overlying said ears, and waist elastic members secured to said backing sheet along end edges to define waist seals with said waist elastic members overlying said ears and overlying and bonded to said side elastic members, said crotch seals and said waist seals cooperating to place direct initial stress and stretch on said waist seals and crotch seals respectively and to hold said ears in a raised position, said side members and said waist members being waterproof forming fluid seals, said adhesive means extending substantially the full length of said backing sheet for preventing pulling apart of said diaper and shifting the balling of said absorbent pad, said waist elastic members extending beyond the side edges of said diaper forming elastic extensions for fastening said diaper on an infant, said extensions having adhesive means for securement to the diaper and being held in a raised position for facilitating placing a diaper on an infant.

* * * * *